Figure 1:
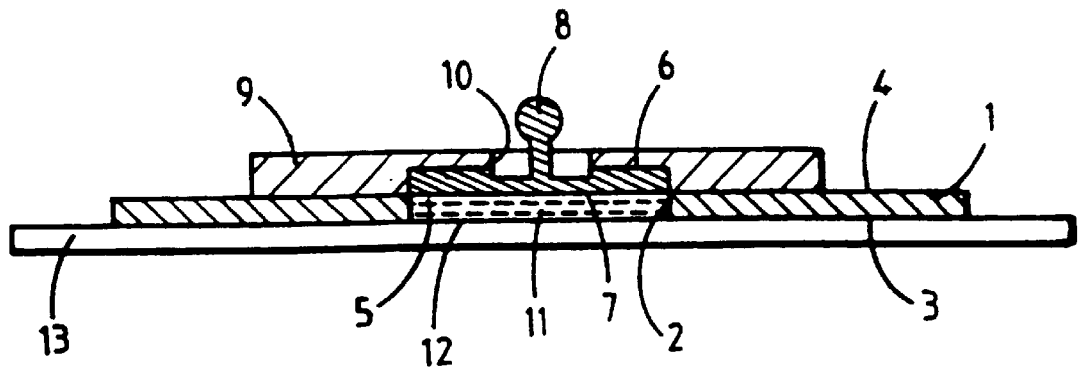

United States Patent [19]
Muller et al.

[11] Patent Number: 6,064,908
[45] Date of Patent: May 16, 2000

[54] DEVICE FOR IONOPHORESIS COMPRISING AT LEAST A MEMBRANE ELECTRODE ASSEMBLY, FOR THE TRANSCUTANEOUS ADMINISTRATION OF ACTIVE PRINCIPLES TO A SUBJECT

[75] Inventors: Daniel Muller, Pau; Frederic Perie, Billere; Alain Barbier, Saint Clement de Riviere, all of France

[73] Assignees: Elf Aquitaine; Sanofi, both of France

[21] Appl. No.: 09/284,971

[22] PCT Filed: Nov. 6, 1997

[86] PCT No.: PCT/FR97/01997

§ 371 Date: Jul. 8, 1999

§ 102(e) Date: Jul. 8, 1999

[87] PCT Pub. No.: WO98/19735

PCT Pub. Date: May 14, 1998

[30] Foreign Application Priority Data

Nov. 7, 1996 [FR] France .................................. 96 13583

[51] Int. Cl.⁷ ...................................................... A61N 1/30
[52] U.S. Cl. .................................................................. 604/20
[58] Field of Search .......................... 604/20, 501, 890.1, 604/19, 21; 607/149, 152, 153, 115; 424/449; 435/173.4, 173.5

*Primary Examiner*—Wynn Wood Coggins
*Assistant Examiner*—Manuel Mendez
*Attorney, Agent, or Firm*—Bacon & Thomas, PLLC

[57] ABSTRACT

The device for ionophoresis combines a donor electrode assembly, a counter electrode assembly and a generator of electricity. The donor assembly comprises a primary reservoir element containing the active principle and a secondary reservoir element containing a neutral electrolyte, these reservoir elements being separated by a semipermeable membrane in polymer material in contact with each of them, and an electrode in contact with the secondary reservoir element. The polymer material of the membrane consists at least in polyethyerblocamide with an Mn between 10000 and 300000 and containing by weight, 35% to 90% of polyamide sequences. The invention is applicable to the transcutaneous administration of active principles to a subject with improved efficiency.

44 Claims, 1 Drawing Sheet

DEVICE FOR IONOPHORESIS COMPRISING AT LEAST A MEMBRANE ELECTRODE ASSEMBLY, FOR THE TRANSCUTANEOUS ADMINISTRATION OF ACTIVE PRINCIPLES TO A SUBJECT

The invention relates to an iontophoresis device for transcutaneous administration of active principles to a subject, which device comprises at least one electrode assembly equipped with a membrane. It furthermore concerns the said electrode assembly.

In the current treatment of numerous conditions, it is necessary to administer a medication or other active principle to a subject in a controlled and often prolonged manner. Amongst the numerous techniques available to the formulation pharmacist, that of iontophoresis represents an advantageous alternative for controlling the administration of active principles such as medicinal substances into the subject's body. One such technique consists in using an electric current for controlling the quantity and also the speed of delivery of an active principle through a subject's skin. In numerous cases, this technique proves highly effective by significantly increasing the supply of active principle due to the current, in comparison to the quantity delivered without a current.

The transcutaneous administration of an active principle by iontophoresis to a subject is generally performed, starting with an aqueous solution or aqueous gel containing the active principle in an at least partially ionized form or in a neutral form, by applying an electric signal between, on the one hand, a first electrode called the active electrode, having the same polarity as the ions of the active principle to be administered or a positive polarity if the active principle is neutral, and being in contact with a reservoir element, which contains the active principle and is placed in contact with a first area of the subject's skin, and, on the other hand, a second electrode called the back electrode or passive electrode, of opposite polarity to that associated with the active principle, which is placed, directly or via an arbitrary electrolyte, in contact with a second area of the subject's skin which is separate from the first area. During the flow of current generated by applying a voltage between the electrodes, in the circuit thus produced, the ions of the active principle migrate away from the electrode of the same polarity (active electrode), through the subject's skin and tissues towards the electrode of opposite polarity (back electrode) and thus find themselves passing through the subject's circulatory system. In the same way, the active principle neutral molecules are entrained, away from the positive electrode, in the aqueous electroosmotic flux through the subject's skin and tissues towards the negative electrode (back electrode) and thus find themselves passing through the subject's circulatory system.

One iontophoresis device for transcutaneous administration of an active principle to a subject is of the type comprising a first electrode assembly consisting of a first electrode called the active electrode, in contact with an active reservoir element, designed, on the one hand, to contain an electrolyte containing the active principle in an at least partially ionized form or in a neutral form and, on the other hand, in order to ensure, when it is placed in contact with an area of the subject's skin, ionically conducting continuity between the said first electrode and the said area, a second electrode assembly consisting either (i) of a second electrode, called the back electrode, or preferably (ii) of a second electrode of this type in contact with a reservoir element designed to contain an electrolyte and to ensure, when it is placed in contact with a portion of the subject's skin, ionically conducting continuity between the second electrode and the said portion and an electric signal generator which can be connected to each of the said first and second electrodes in such a way that the first electrode has the same polarity as the ions of the active principle or a positive polarity if the said active principle is neutral and that the second electrode has a polarity opposite to that of the first electrode.

Citation WO-A-9116943 relates to an iontophoresis device containing at least one donor electrode assembly, that is to say an electrode assembly containing an active principle to be administered, the said donor assembly comprising an electrode, for example a reversible electrode based on zinc, silver and/or silver chloride, a primary reservoir element, designed, on the one hand, to contain an electrolyte containing the active principle to be administered in an at least partially ionized form or in a neutral form and, on the other hand, in order to ensure, when it is placed in contact with an area of the subject's skin, ionically conducting continuity between the said electrode and the said area, and a membrane in contact, via one of its faces, with the electrode and, via its other face, with the primary reservoir element, the said membrane being selectively permeable to ions and molecules of sizes smaller than a chosen threshold, in order to stop the ions and molecules of the active principle from passing through the membrane.

In one variant, the donor electrode assembly also comprises a secondary reservoir element containing an arbitrary electrolyte, the said secondary reservoir element being arranged between the electrode and the membrane so as to be in contact with each of them.

The presence of a membrane selectively permeable to ions and molecules of sizes smaller than those of the ions and molecules of the active principle in the donor electrode assembly of an iontophoresis device, in order to separate the primary reservoir element containing the active principle from the electrode or the secondary reservoir element in contact with the electrode, makes it possible to confine the active principle in the primary reservoir element and thus prevent the said active principle from coming into contact with the electrode and either being absorbed on the said electrode, with the result of a substantial increase in the resistivity of the iontophoresis device, or suffering degradation due to reactions with the electrode or catalysed by the electrode. Furthermore, the membrane prevents migration towards the electrode of ionized products such as lipids and fats, which tend to pass from the blood medium and the skin into the electrode assemblies of the iontophoresis device when the latter is in operation. Finally, the presence of the membrane also makes it possible to prevent the counter-ions of the active principle from coming into contact with the electrode and corroding it and/or degrading it.

The selectively permeable membranes used in citation WO-A-9116943 may be made of a homogeneous material consisting of a polymer or a mixture of compatible polymers, or of a heterogeneous material consisting of a polymer material supplemented by a pore-forming agent such as polyethylene glycol. The polymers which can be used to form the said membranes may be like polycarbonates, polyvinyl chloride, polyamides, halogenated polymers, polysulphones, polyacetals, thermoplastic polyethers, acrylic resins, polyurethanes, polyimides, polybenzimidazoles, polyvinyl acetate, cellulose esters, hydroxylated or carboxylated celluloses, epoxy resins, polyolefins, crosslinked polyoxyethylenes, crosslinked polyvinyl alcohols, crosslinked polyvinylpyrrolidones, and ethylene/vinyl acetate copolymers. One preferred material consists of cellulose acetate containing up to 20% of a pore-forming agent consisting of polyethylene glycol with molecular mass in the 400 to 8000 range.

Many membranes made of polymer material, in particular of polyvinyl chloride, ethylene/vinyl acetate copolymer, polyamide, polyolefin, polyacetals, and epoxy resin, have relatively high impedance, which results, during operation of the iontophoresis device including the membrane, in an extra loss of electrical energy through the Joule effect.

The membranes which are obtained from strongly hydrophilic polymers, for example crosslinked polyoxyethylenes, crosslinked acrylic acid polymers, hydroxylated or carboxylated and crosslinked celluloses, have low impedance but swell significantly in the presence of water and have poor long-term stability when they are swollen with water.

As for the porous membranes obtained from a polymer material containing a pore-forming agent, for example cellulose acetate containing a polyethylene glycol oligomer, they exhibit a structural heterogeneity which, in particular, leads to mechanical characteristics which are not always satisfactory, and have poor long-term impermeability in respect of wet storage.

It has now been found that, by choosing as membrane constituent material a polymer material consisting of at least one polyether block amide (polyether ester amide) of particular composition, a membrane is obtained which proves particularly effective as a selectively permeable membrane for an electrode assembly of an iontophoresis device.

More particularly, the membrane according to the invention has low impedance, in most cases less than 1 kohm/cm$^2$, excellent mechanical strength and high long-term stability. The said membrane is impermeable to liquid water, withstands sterilization as well as radiosterilization and offers perfect resistance to all the agents, in particular alcohols and glycols, promoting transcutaneous passage of the active principle. It is highly permeable to water vapour, which allows very rapid hydration in the case of reservoir elements for active principle or electrolyte which are fitted in the dehydrated state, and presents a good compromise between its barrier properties and its wet conductivity. It can undergo long-term storage in a wet environment. This membrane can be obtained at low cost, from polyether block amides which do not contain any stabilizer of ionic or toxic nature and have obtained pharmaceutical approval. Finally, such a membrane adheres well to most pharmaceutical self-adhesives, dry or in the wet state, and can be heat-sealed with numerous materials, including those forming the framework of the iontophoresis device holding it.

The invention therefore relates to an improved iontophoresis device comprising at least one donor electrode assembly equipped with a selectively permeable membrane made of a polymer material consisting of at least one polyether block amide with specific characteristics. It also concerns the said electrode assembly.

The iontophoresis device according to the invention, for transcutaneous administration of an active principle to a subject, is of the type comprising (a) a first electrode assembly (called the donor electrode assembly) consisting of a first electrode (called the active electrode), a primary reservoir element, designed, on the one hand, to contain a primary electrolyte medium containing the active principle in an at least partially ionized form or in a neutral form and, on the other hand, in order to ensure, when it is placed in contact with an area of the subject's skin, ionically conducting continuity between the said first electrode and the said area, and a membrane made of polymer material in contact, via one face, with the first electrode and, via another face, with the primary reservoir element, the said membrane being selectively permeable to ions and molecules of sizes smaller than a chosen threshold, in particular in order to prevent the neutral or ionized active principle from passing through the membrane, (b) a second electrode assembly consisting either (i) of a second electrode, called the back electrode, or preferably (ii) of a second electrode of this type in contact with a reservoir element, called back-electrode reservoir, designed to contain at least one electrolyte medium and to ensure, when it is placed in contact with a portion of the subject's skin, ionically conducting continuity between the second electrode and the said portion and (c) an electric signal generator which can be connected to each of the said first and second electrodes in such a way that the first electrode has the same polarity as the ions of the active principle or a positive polarity if the said active principle is neutral and that the second electrode has a polarity opposite to that of the first electrode, the said device being characterized in that the polymer material constituting the selectively permeable membrane consists of at least one polyether block amide formed by identical or different units corresponding to the formula

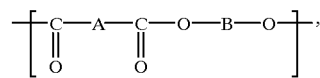

in which A is a polyamide sequence derived, by losing its COOH groups, from a dicarboxylic polyamide having a COOH group at each of the ends of its chain, and B is a polyoxyalkylene sequence derived, by losing two hydroxyl groups, from a polyoxyalkylene glycol whose chain is formed by oxyalkylene units having 2 to 4 carbon atoms and has an OH group at each of its ends, the said polyether block amide having a number-average molecular mass of between 10,000 and 300,000, preferably between 10,000 and 200,000 and more especially between 15,000 and 100,000, and containing a proportion by weight of polyamide sequences A of between 35% and 90% and preferably between 45% and 85%.

The invention also relates to a donor electrode assembly, for an iontophoresis device, of the type comprising an active electrode, a primary reservoir element, designed, on the one hand, to contain a primary electrolyte medium containing the active principle in an at least partially ionized form or in a neutral form and, on the other hand, in order to ensure, when it is placed in contact with an area of the subject's skin, ionically conducting continuity between the said active electrode and the said area, and a membrane made of polymer material in contact, via one face, with the active electrode and, via another face, with the primary reservoir element, the said membrane being selectively permeable to ions and molecules of sizes smaller than a chosen threshold, in particular in order to prevent the neutral or ionized active principle from passing through the membrane, the said donor electrode assembly being characterized in that the polymer material constituting the selectively permeable membrane consists of at least one polyether block amide having the definition given above.

The dicarboxylic polyamides HOOC—A—COOH, which have a COOH group at each of the ends of their chains and from which the polyamide sequence A of the units

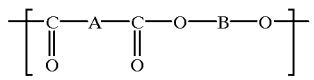

constituting the polyether block amide forming the polymer material of the membrane derives, are obtained as is well known in the art, for example, by polycondensation of one or more lactams and/or one or more amino acids or by polycondensation of a dicarboxylic acid with a diamine, these polycondensations being carried out in the presence of an excess of an organic dicarboxylic acid whose carboxylic functions are preferably bound to each of the ends of the acidic molecule. These dicarboxylic acids become bound during the polycondensation as constituents of the macromolecular chain of the polyamide and, in particular, to the ends of this chain, which makes it possible to obtain a dicarboxylic polyamide having a COOH group at each of the ends of its chain.

The dicarboxylic polyamide HOOC—A—COOH mentioned above can thus be obtained by polycondensation, in the presence of a dicarboxylic acid having 4 to 20 and preferably 5 to 12 carbon atoms in its molecule, of one or more monomers selected from the group formed by lactams and amino acids having 4 to 16 and preferably 5 to 12 carbon atoms in their molecules and the combinations of one or more diamines having 4 to 16 and preferably 5 to 12 carbon atoms in their molecules with one or more dicarboxylic acids having 4 to 18 and preferably 5 to 12 carbon atoms in their molecules. In particular, the dicarboxylic polyamides may be obtained from one or more monomers chosen from caprolactam, oenantholactam, dodecalactam, undecanolactam, decanolactam, 11-amino undecanoic acid and 12-amino dodecanoic acid, for example polyamide-6, polyamide-11, polyamide-12, copolyamide-6/11 or -6/12, or may be produced by polycondensation of hexamethylene diamine with adipic acid, azelaic acid, sebacic acid or 1,12-dodecanedioic acid, the corresponding polyamide sequences being known by the names nylon-6,6, -6,9, -6,10 or -6,12, or by polycondensation of nonamethylene diamine with adipic acid to form a polyamide sequence known under the name nylon-9,6.

The dicarboxylic acids having 4 to 20 and preferably 5 to 12 carbon atoms in their molecule, which are used in the reaction for synthesizing the dicarboxylic polyamide, on the one hand, in order to make it possible to bind a COOH group to each of the ends of the polyamide chain and, on the other hand, as chain limiters, may advantageously be alkanedioic acids such as, for example, succinic, adipic, suberic, azelaic, sebacic, undecanedioic and dodecanedioic acids, or cycloaliphatic or aromatic dicarboxylic acids such as, for example, terephthalic, isophthalic or cyclohexane-1,4-dicarboxylic acids. These dicarboxylic acids are employed in excess in the proportion needed to obtain a polyamide of the desired molecular mass using conventional calculations for the polycondensation technique.

The number-average molecular masses of the sequences A derived from the dicarboxylic polyamides can vary in a fairly wide range, the said range lying advantageously between 300 and 15,000 and preferably between 800 and 6000.

The polyoxyalkylene glycols with hydroxyl end groups, from which the sequence B of the units

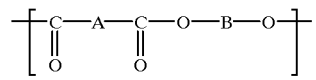

constituting the polyether block amide forming the polymer material of the membrane derives, are advantageously polymers consisting of one or more of the repeat units

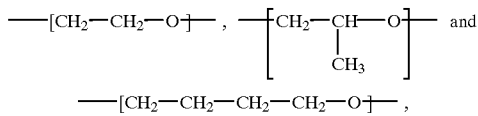

in particular polyoxyethylene glycols, polyoxypropylene glycols, polyoxytetramethylene glycols, copoly(oxyethylene/oxypropylene) glycols, copoly(oxyethylene/oxytetramethylene) glycols, copoly(oxyethylene/oxypropylene/oxytetramethylene) glycols and mixtures of such polyoxyalkylene glycols and/or their copolymers.

The number-average molecular masses of the sequences B derived from the polyoxyalkylene glycols with hydroxyl end groups can vary fairly widely, for example between 100 and 6000, and more particularly lie between 200 and 3000.

The polyether block amide may be obtained by polycondensation of the dicarboxylic polyamide HOOC—A—COOH and the polyoxyalkylene glycol HO—B—OH in the presence of the dicarboxylic acid chosen as chain limiter, proceeding in the molten state in contact with a catalyst consisting of a titanium, zirconium or hafnium tetraalkoxide. For further details about this synthesis, reference may be made in particular to the citations FR-A-2273021 (titanium catalyst) and FR-A-2401947 (zirconium or hafnium catalyst).

The thickness of the polyether block amide membrane may advantageously vary between 10 $\mu$m and 200 $\mu$m, and more particularly lies between 12 $\mu$m and 100 $\mu$m.

The primary reservoir element of the first electrode assembly, or donor electrode assembly, has a thickness which is advantageously between 50 $\mu$m and 1000 $\mu$m and more particularly lies between 100 $\mu$m and 600 $\mu$m.

In an advantageous embodiment of the iontophoresis device, the first electrode assembly or donor electrode assembly is also provided with a secondary reservoir element containing an arbitrary electrolyte, the said secondary reservoir element being arranged between the electrode of the said assembly and the polyether block amide membrane so as to be in contact with each of them.

The said secondary reservoir element has a thickness which can vary, for example, between 100 $\mu$m and 4 mm. The volume of this secondary reservoir element is advantageously greater than or equal to the volume of the primary reservoir element and more particularly lies between 1 times and 12 times the volume of the said primary reservoir element.

The electrode of the first electrode assembly, that is to say the active electrode of the donor electrode assembly, as well as the electrode of the second electrode assembly may be made of a metal or metal alloy such as titanium, platinum, stainless steel or of a nonmetallic electronically conducting material such as carbon or graphite. Advantageously, at least the electrode of the first electrode assembly, that is to say the active electrode of the donor electrode assembly, and preferably the electrode of each of the first and second electrode assemblies is a consumable electrode, that is to say an electrode containing an electrochemically consumable material, which is consumed, by electrochemical oxidation or reduction depending on the case, when the current flows during operation of the iontophoresis device.

The consumable electrode may be of the cathode type or of the anode type. In a consumable electrode of the cathode type, the consumable material is consumed by reduction. Such a consumable cathode may advantageously be chosen from ionizable metal compounds whose metal ions can be reduced electrochemically to the corresponding metal. Examples of these metal compounds which may be mentioned, without implying any limitation, include the compounds AgCl and CuCl. In particular, the consumable cathode may be formed by combining the metal compound with the metal corresponding to it so as to form, at least during operation of the device, a reversible electrode. The consumable material of the cathode may be deposited on a support, which support may consist of an insulating material and, in particular of an insulating plastic material such as polypropylene, polyethylene, PVC, polyester or of a metallic or nonmetallic electronically conducting material which withstands corrosion by the electrolyte in contact with the electrode in the absence of current such as, for example, silver, titanium, platinum, stainless steel, carbon, graphite, or conducting polymer.

In a consumable electrode of the anode type, the electrochemically consumable material is consumed by oxidation. Such a consumable anode may consist, at least in part, of a metal such as, for example, Al, Cu, Mg, Zn and Ag. In this case, the said metal which can be consumed by electrochemical oxidation may in particular be chosen from those, such as silver, which can form an electrochemically reversible system with the metal ions resulting from the electrochemical oxidation so as to form a reversible anode during the operation of the device. The material of the anode which can be consumed by electrochemical oxidation may be deposited on a support consisting of an insulating material and, in particular, of an insulating plastic material such as polypropylene, PVC, polyethylene, polyester or of a metallic or nonmetallic electronically conducting material such as, for example, titanium, platinum, stainless steel, carbon, graphite, or conducting polymer.

The cathode and/or anode may be designed to form composite electrodes formed by a composition based on a polymer binder, a conductive powder or fibre filler, in particular carbon black or short graphite fibres, and the consumable material of the electrode in a divided form, namely, in the case of the cathode, the electrochemically reducible metal compound on its own or in combination with the corresponding metal and, in the case of the anode, metal or metal alloy chosen to form the said anode. The polymer binder is preferably a polymer based on 1,2-epoxy propane and/or 1,2-epoxy butane as described in citation FR-A-2722993.

According to one embodiment of the iontophoresis device according to the invention, which makes it possible to administer transcutaneously a given total quantity of an active principle to a subject, one or other of the cathode and anode is designed to form an electrode, called the limiting electrode, formed by a limited quantity of an electrochemically consumable material combined either with an electronically conducting support or an insulating support, the said electrochemically consumable material being either an electrochemically reducible metal compound when the limiting electrode is a cathode or a metal consumable by electrochemical oxidation, in particular a metal such as Al, Mg, Zn or Ag, when the limiting electrode is an anode, and the said electronically conducting support being made of a material which resists corrosion by the electrolyte associated with the limiting electrode in the absence of current and which has, when the limiting electrode is a cathode, a hydrogen overpotential in the presence of the said electrolyte at least equal to that of aluminium or which is not consumable by electrochemical oxidation when the limiting electrode is an anode, while the said limited quantity of electrochemically consumable material is chosen so that the quantity of electricity needed to consume it electrochemically corresponds to the quantity of electricity needed to administer the given total quantity of active principle to the subject, so that the flow of current between the electrodes (anode and cathode) is substantially interrupted when the consumable material of the limiting electrode has been consumed, and the active principle is initially present in the primary reservoir element in contact with the associated electrode in a quantity greater than the given total quantity to be administered to the subject.

A particular example of a suitable insulating support for the limiting electrode is a support made of an insulating plastic material such as polypropylene, polyethylene, PVC or polyester.

As an electronically conducting support for the limiting cathode, use may advantageously be made of a support made of a material chosen from aluminium, silver, titanium, tantalum, vanadium, stainless steel, zinc, carbon, graphite and a conducting polymer. An example of a suitable conducting support for the limiting anode is a support made of a material chosen from platinum, titanium, stainless steel, gold, carbon, graphite and a conducting polymer.

The metallically conducting supports of the electrodes, anode or cathode, may be in bulk form or consist of very thin metal deposits on insulating plastic films. These metal deposits may be formed by any known technique such as, for example, vacuum metallization or cathode sputtering.

By way of nonlimiting examples of electrodes which can be used as nonlimiting or limiting cathodes in the device according to the invention, mention may be made of electrodes based on AgCl or CuCl on a support consisting of the corresponding metal or a support made of stainless steel, carbon, polypropylene, polyethylene or a conducting polymer. As examples of nonlimiting or limiting consumable anodes in the device according to the invention, mention may be made, by way of nonlimiting example, of nonlimiting electrodes based on a metal which can be consumed by electrochemical oxidation chosen from Al, Ag, Cu, Mg and Zn and limiting electrodes based on such a metal deposited on an insulating support such as polypropylene, polyethylene or polyester or on a support chosen from titanium, stainless steel, platinum, carbon, graphite or a conducting polymer.

As indicated above, the electrochemically consumable material of the limiting electrode is present in the said electrode in a quantity such as the quantity of electricity needed for it to be consumed electrochemically corresponds to the quantity of electricity to be used for administering the given total quantity of the active principle to the subject. This latter quantity of electricity, which depends on the iontophoresis system used, that is to say the reaction media in contact with the cathode and the anode, on the electric signal applied to the electrodes and on the nature of the said electrodes, will be determined by means of preliminary tests for each type of iontophoresis system employed.

The electrical generator applies between the electrodes, active electrode and back electrode of the iontophoresis device an electric signal which may be either an intensiometric signal, that is to say a signal with an average intensity which is set and, for example, constant (intensiostatic signal), or, preferably, a potentiometric signal, that is to say a signal with an average voltage which is set, for example constant (potentiostatic signal). The electric signal of intensiometric type or of potentiometric type may be continuous or pulsed and permanent or intermittent, with or without temporary polarity inversion. Its frequency may range from 0 (continuous signal) to 500 kHz and more particularly from 0 to 100 kHz. When the electric signal is of a pulsed type, it may have a duty cycle, that is to say a ratio between the duration of the elementary pulse, whose repetition forms the pulsed signal, and the time interval separating two successive appearances of this pulse, ranging from 0.05 to 0.95 and more particularly from 0.1 to 0.8.

Advantageously, the average voltage of the signal applied by the generator between the cathode and the anode is chosen between 0.1 and 50 volts and more especially between 0.3 and 20 volts so that the density of the average current generated between the said electrodes (cathode and anode) has a value less than 0.5 mA/cm$^2$, more particularly between 0.05 and 0.3 mA/cm$^2$ and very especially between 0.05 and 0.2 mA/cm$^2$.

The electric signal generator of the device according to the invention may be of any known type making it possible to generate electric signals of set average intensity or set average voltage or signals of both types, which are continuous or pulsed and permanent or intermittent, with or without temporary polarity inversion, and which have the characteristics defined above.

The primary electrolyte medium, which is present in the primary reservoir element of the first electrode assembly or donor electrode assembly, may consist of an aqueous solution or of an adhesive or nonadhesive hydrogel containing the active principle to be administered in an at least partially ionized form or in a neutral form. The primary reservoir element may also be in the form of a hydratable solid consisting of a self-adhesive or non-self-adhesive matrix made of a hydrophobic polymer material in which one or more water-soluble or hydrophilic polymers and the active principle to be administered are dispersed. In this form, the primary reservoir element will need to be hydrated at the time when the iontophoresis device is used. The concentration of active principle in the aqueous phase (aqueous solution or hydrogel) contained in the primary electrolyte medium of the primary reservoir element is advantageously between 0.2% by weight of the aqueous phase and the saturation concentration of the said aqueous phase.

The arbitrary electrolyte contained in the secondary reservoir element of the first electrode assembly, or donor electrode assembly, may consist of an aqueous solution or a hydrogel containing one or more pharmaceutically acceptable salts which can be ionized in the aqueous phase. The said salts will, in particular, be salts of alkali or alkaline earth metals such as chlorides, for example NaCl, sulphates, carbonates, nitrates, phosphates, ascorbates, citrates, acetates and mixtures of such salts. It is also possible to produce the secondary reservoir element containing the arbitrary electrolyte medium in the form of a hydratable solid formed by a hydrophobic polymer matrix in which one or more hydrophilic polymers and the ionizable salt or salts are dispersed, or consisting of a hydrophilic absorbent matrix, for example filter paper, containing the ionizable salt or salts in the dispersed state. Such reservoir elements are prepared in the absence of water and need to be hydrated at the time when the iontophoresis device is used.

Similarly, the electrolyte medium contained in the reservoir element of the second electrode assembly may consist of an aqueous solution or of a hydrogel containing one or more pharmaceutically acceptable salts which can be ionized in the aqueous phase, of the same type as the salts present in the arbitrary electrolyte contained in the secondary reservoir element of the first electrode assembly.

It is also conceivable to form the reservoir element of the second electrode assembly in the form of a hydratable solid as indicated for the secondary reservoir element.

Examples of aqueous gels or thick aqueous solutions are in particular described, respectively, in citations U.S. Pat. Nos. 4,766,164 and 3,163,166. Reservoirs of active principle or only arbitrary electrolyte which are in the form of hydratable solids are described, for example, in citation WO-A-9116943.

The primary electrolyte medium containing the active principle, as well as the electrolyte medium of the reservoir element of the second electrode assembly, may, if need be, contain agents capable of promoting the transcutaneous passage of the active principle, such as, for example, vasodilators and/or amphiphilic agents, nonlimiting examples of which include compounds of the alcohol type and of the ester type. These agents are used in concentrations allowing good solubility of the active principle in the medium.

The active principle to be administered may be introduced not only into the primary reservoir element of the first electrode assembly, but also into the reservoir element of the second electrode assembly, giving the second electrode assembly a structure similar to that of the first electrode assembly and forming the electrode of each of the electrode assemblies by a reversible consumable electrode, for example a reversible electrode based on the Ag/AgCl pair. This makes it possible, by reversing the polarity of the electric signals applied to the electrodes, to administer the active principle alternately from the primary reservoir element of the first electrode assembly and from the corresponding reservoir element of the second electrode assembly.

The iontophoresis device according to the invention may be produced on the basis of any known iontophoresis device, by arranging at least the electrode assembly of the said device, which contains the active principle, so as to give it a structure corresponding to the structure, with or without secondary reservoir element, of the first electrode assembly, equipped with a polyether block amide membrane, of the device according to the invention, the electrodes being preferably consumable electrodes and more particularly reversible electrodes, for example electrodes based on the Ag/AgCl pair, with, optionally, one of the electrodes designed to form a limiting consumable electrode.

In particular, the device according to the invention may be a portable, self-contained device, to be fixed using a bracelet or possibly to be bonded adhesively to the skin, comprising electrodes which each have an area less than 50 cm$^2$ and more particularly between 1 cm$^2$ and 30 cm$^2$, and a miniaturized electric signal generator. A self-contained, portable device according to the invention may thus have a structure similar to that of the self-contained, portable iontophoresis devices described, for example, in citations U.S. Pat. No. 4,325,367, EP-A-0060452 and FR-A-2509182, on condition that at least the electrode assembly of the said device which contains the active principle has a structure corresponding to that of the first electrode assembly with polyether block amide membrane, with or without secondary reservoir element, of the device according to the invention. The cathode may, for example, be an electrode based on AgCl or CuCl on a silver, copper, carbon, polypropylene or polyethylene support or a conducting polymer. The anode may be a conventional anode, for example an anode made of metal or metal alloy such as titanium, platinum, stainless steel, or a nonmetallic electronically conducting material such as carbon or graphite, or a nonreversible or reversible consumable anode, for example an anode made of a metal such as Al, Cu, Mg, Zn and Ag, where appropriate deposited on an insulating support such as polypropylene or polyester or on a support chosen from titanium, stainless steel, platinum, carbon, graphite and conducting polymer. The said anode and cathode, one or other of which may be designed as indicated above to form a limiting electrode, each have an area less than 50 cm$^2$ and more particularly between 1 and 30 cm$^2$.

When the first electrode assembly and the second electrode assembly are fixed to the skin using an adhesive, this may be done by providing a layer of an ion-conducting adhesive on the face, intended to come into contact with the skin, of the reservoir element of each electrode assembly or an area surrounding the said face.

The iontophoresis device according to the invention, when it is equipped with at least one electrode based on the Ag/AgCl pair and, preferably, comprises an anode and a cathode based on the said Ag/AgCl pair, may also include an assembly for monitoring the degree of progress of the transcutaneous administration of the active principle, as described in citation FR-A-2724115.

According to the invention, it is possible to produce the electrode assembly containing the active principle (first electrode assembly or donor electrode assembly) by producing the primary reservoir element and, if it is used, the secondary reservoir element in the form of hydratable solids, as indicated above, then assembling dry the said reservoir elements, the membrane and the electrode to form the electrode assembly in the nonhydrated state. It is in the same way possible to produce, in the form of a hydratable solid, the reservoir element of the second electrode assembly and assemble dry the said reservoir with the associated electrode (back electrode) to form the second electrode assembly in the nonhydrated state. The said first and second electrode assemblies are hydrated only when the iontophoresis device is set in operation.

The selectively permeable membrane present in the electrode assembly containing the active principle (first electrode assembly or donor electrode assembly) substantially prevents the migration of ions and molecules which have molecular masses higher than 100 daltons and more especially higher than 300 daltons. The presence of this membrane in contact with the primary reservoir element containing the active principle makes it possible to confine the said active principle in the primary reservoir element and thus prevent it from being diluted in the secondary reservoir element, if it is present, and from being degraded in contact with the electrode of the electrode assembly.

The iontophoresis device according to the invention makes it possible to administer various active principles to a subject by transcutaneous means. It is particularly effective for administering cationic or anionic active principles derived from therapeutic molecules having molecular masses higher than 100 daltons such as, for example, insulin, metoprolol, hydrocodone, tetracyclines, salbutamol, valproic acid, propanolol, arginine-desmopressine, fentanyl or others, or such as those mentioned in citation WO-A-9116943 (cf. page 24, line 1, to page 25, line 18). The device according to the invention is advantageously usable for administration of active principles, in particular anionic active principles, with high molecular masses, that is to say higher than 300 daltons. As examples of such active principles, mention may be made of the alkali metal or alkaline earth metal salts, in particular sodium salts, of oligosaccharides, whose iontophoretic administration is proposed in citation FR-A-2729574 and which consist of two to twelve saccharide units, some or all of which have their OH groups replaced, at least in part, by functional groups chosen from $—OSO_3^-$, $—COO^-$, $—NHSO_3^-$, $—NH$-acyl, $—OPO_3^{--}$ and $—OT$, T being a hydrocarbon radical and which have an ionic nature appropriate for iontophoretic administration, the said oligosaccharides being more especially tri-, tetra-, penta- or hexasaccharides and very particularly pentasaccharides. As other examples of the said active principles, mention may also be made of anionic glycosaminoglycans, whose iontophoretic administration is proposed in citation FR-A-2729575 and which consist of alkali metal or alkaline earth metal salts, in particular sodium, potassium or calcium salts, of anionic glycosaminoglycans whose mucopolysaccharide chains have molecular masses of between 1000 and 15,000 and more especially between 2500 and 10,000, the said anionic glycosaminoglycans being in particular heparins whose mucopolysaccharide chains have low molecular masses, that is to say molecular masses as defined above.

The invention is illustrated by the following examples given without implying any limitation.

EXAMPLE 1

Study of the transdermic passage of a pentasaccharide sodium salt by iontophoresis at set intensity.

The pentasaccharide used corresponded to that having the formula given below:

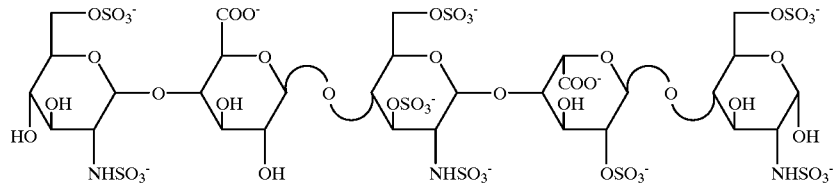

Prior to the tests on transdermic passage of the pentasaccharide, on the one hand the impedances (resistance) and, on the other hand, the passive permeability and permeability under iontophoresis to the pentasaccharide were determined for a series of membranes including membranes according to the invention, formed from films of two polyether block amides marketed by the company ELF ATOCHEM under the names PEBAX® MV 1041 and MV 1074, and membranes according to the prior art formed from films of cellulose acetate, polyamide-11 or a mixture of cellulose acetate and 10% by weight of polyoxyethylene glycol (POEG) with molecular mass equal to 400.

PEBAXs MV 1041 and MV 1074 are polyether block amides whose A sequences consist of a polyamide-12 with number-average molecular mass $\overline{M}_n$ equal to 4500 (PEBAX MV 1041) or 1500 (PEBAX MV 1074) and whose B sequences consist of a polyoxyethylene with $\overline{M}_n$ equal to 1500, the said polyether block amides having an $\overline{M}_n$ of about 24,000 (PEBAX MV 1041) or about 21,000 (PEBAX MV 1074) and a proportion by weight of polyamide equal to 75% (PEBAX MV 1041) or 50% (PEBAX MV 1074).

The permeability of the membranes to the pentasaccharide under iontophoresis was determined by using an iontophoresis device comprising a donor compartment and a receiver compartment which are separated from one another by the membrane to be studied, the donor compartment containing the pentasaccharide in the form of a 2% by weight aqueous solution and being equipped with a cathode based on chloridized silver (Ag/AgCl cathode), and the receiver compartment containing a 9 g/liter aqueous solution of NaCl and also being equipped with an anode based on chloridized silver. Working at controlled intensity (0.2 mA/cm$^2$), a quantity of electricity corresponding to 2 mAh was applied to the system, the said application being carried out in 5 hours.

The passive permeability of the membranes to the pentasaccharide was determined by using a device comparable with the one described above, but without an electrode.

In each of the determinations mentioned above, samples of the liquid contained in the receiver compartment were taken after determined durations and, by assaying the antifactor Xa activity of the said samples, the quantity of pentasaccharide which has passed into the receiver compartment through the membrane was obtained.

The results obtained are presented in Table IA given below.

TABLE IA

| Material of the membrane | Resistance for various thicknesses (kΩ) | | | | Permeability for a 50 µm thickness | |
|---|---|---|---|---|---|---|
| | | | | | Passive over 1 month (µg/cm$^2$) | Iontophoresis over 24 h/ 2 mAh (µg/cm$^2$) |
| | 25 µm | 50 µm | 75 µm | 100 µm | | |
| PEBAX MV 1041 | 0.3 | 0.8 | | 3 | <2 | <5 |
| PEBAX MV 1074 | 0.25 | 0.6 | | 2 | 4 | 6 |
| Cellulose acetate | 40 | 80 | 140 | 190 | <2 | |
| Polyamide-11 | | 220 | >1000 | | ~0 | |
| Mixture of cellulose acetate/10% POEG | | 4 | 6 | 8.5 | 12 | 30 |

Reading Table IA, it can be seen that the membranes formed by films of polyamide-11 or cellulose acetate cannot be used in iontophoresis because their impedance is too high and they would therefore lead to Joule effect losses which are too great for a lightweight, portable iontophoresis device. It should also be noted that although the membranes obtained from the cellulose acetate/POEG (10%) mixture have a lower impedance than the membranes formed from pure cellulose acetate films, they are much more permeable, even passively, which is likely to lead to rapid dilution of the active principle in the two reservoirs of the electrode assembly, and thus to a permanent loss of potential performance of the electrode assembly in the event of storage, if the said assembly is not free of water or solvent of the active principle.

The tests on transdermic passage of the pentasaccharide were carried out with membranes according to the invention made of PEBAX MV 1041 or PEBAX MV 1074 having a thickness of 50 µm and, for the purpose of comparison, with 75 µm thick composite membranes obtained from the cellulose acetate/POEG (10%) mixture.

The procedure was carried out in iontophoresis cells with identical structure. Each iontophoresis cell consisted of three coaxial, adjacent cylindrical compartments of 2 cm$^2$ cross section, namely, in this order, a donor compartment, a receiver compartment and a back electrode compartment, these three compartments each being separated from the next in leaktight fashion by a piece of nude rat skin from the same batch, serving as a skin sample for studying the transdermic diffusion. The donor compartment contained a 2% by weight aqueous solution of the sodium salt of the aforementioned pentasaccharide having an antifactor Xa activity of 0.65 "Golden Standard" units per microgram. The receiver compartment, with a volume of 10 ml, contained a 9 g/liter solution of NaCl and was agitated using a magnetic bar. The back electrode compartment, with a volume of 0.5 ml, contained a 2% by weight aqueous solution of NaCl. At its end opposite the receiver compartment, the donor compartment was fitted with a negative electrode or cathode consisting of a 15 µm thick film of silver chloridized on one face to contain an AgCl layer corresponding to 2 mAh/cm$^2$. In the same way as the donor compartment, the back electrode compartment was equipped with a positive electrode or anode (back electrode) consisting of a 15 µm silver film weakly chloridized on the surface (a quantity of AgCl corresponding to 0.1 mAh/cm$^2$). The chloridized face of each electrode was turned towards the rat skin sample.

The rat skin samples had had the subcutaneous tissues removed and were preserved by freezing at −40° C. until they were fitted in the iontophoresis cell, with the dermal faces turned towards the receiver compartment, after having spent 15 minutes in physiological salt solution.

For each of the tests which were carried out, six identical iontophoresis cells were started up simultaneously. The active exchange surface was 2 cm$^2$ for each skin sample.

A current generator, equipped with safety functions preventing it from exceeding a maximum voltage of 5 volts, imparted a direct current of constant strength equal to 0.4 mA, i.e. 0.2 mA/cm$^2$ on the electrodes of each of the six iontophoresis cells. The current produced by the generator was applied for 5 hours, the electrode of the donor compartment of each cell being connected to the negative pole of the said generator, and the back electrodes to the positive pole.

At the end of the said period, an aliquot of the medium contained in the receiver compartment was taken, and the quantity of pentasaccharide which had passed through the skin separating the donor and receiver compartments of each cell was determined by assaying. A second sample was taken 22 hours after the start of each experiment, i.e. 17 hours after the end of the electric signal, in order to allow a significant proportion of the quantities of pentasaccharide active principle held in the skin sample to diffuse in the absence of subcutaneous blood circulation.

Five tests 1a to 1e were carried out as follows:

Test 1a: The donor compartment had a volume of 0.5 ml (5 mg/cm$^2$ of active principle) and no membrane was used.

Test 1b: The donor compartment had a volume of 0.1 ml (1 mg/cm$^2$ of active principle) and no membrane was used.

Test 1c: The donor compartment comprised an active principle reservoir (primary reservoir element) containing 0.1 ml of a 2% by weight aqueous solution of the active principle (1 mg/cm$^2$ of active principle) and separated from an electrode compartment (secondary reservoir element) having a volume of 0.8 ml and containing a 5 g/liter solution of NaCl by a membrane formed by a 75 μm thick film obtained from the aforementioned mixture of cellulose acetate and 10% by weight of POEG with molecular mass equal to 400.

Test 1d: The donor compartment had the same structure as that in Test 1 c, but the membrane consisted of a PEBAX MV 1041 film having a thickness of 50 μm.

Test 1e: The donor compartment comprised an active principle reservoir (primary reservoir element) consisting of a hydrogel based on agarose having a thickness of 250 μm and containing 2% by weight of active principle, i.e. 0.5 mg/cm$^2$ of active principle, separated from an electrode compartment (secondary reservoir element) having a volume of 0.6 ml and containing a 0.5 g/liter aqueous solution of NaCl, by a membrane consisting of a PEBAX MV 1074 film having a thickness of 50 μm.

For each of the tests, the average antifactor Xa activity per ml of medium was determined on aliquots taken from the receiver compartments of the six cells, this representing the quantity of pentasaccharide which had diffused into these compartments after the 5 hours of applying the current and 22 hours after the start of each experiment, i.e. 17 hours after the end of the said current.

The assay of the pentasaccharide in the receiver compartment was based on investigating its antifactor Xa activity. The assay was carried out either directly on the medium sample from the receiver compartment or after dilution, using a ROTACHROM HEPARIN 8® assay kit, with a complementary buffer for the assay instrument and the bovine antithrombin III, these various elements being supplied by the company STAGO, using a HITACHI 717 assay instrument. The calibration curve was established using a "Golden Standard" pentasaccharide solution to which an antifactor Xa activity equal to 13 units per ml was assigned.

The results of the iontophoresis tests and passive administration tests are collated in Table IB.

The data presented in this table are average results calculated over a series of six identical cells receiving the same quantities of electricity. The standard deviations on the mean are generally less than 15%, except for the passive transport in which the standard deviation on the mean reaches close to 35%. All the cells received the same quantity of electricity, apart from the cells in the passive test (passive transport without current) and the cells in Test 1c, for which the generator was at the limit of its capacity and could not provide all the current demanded because of the high impedance of the membranes based on cellulose acetate and POEG which were used in this test.

TABLE IB

| Test | Passive | 1a | 1b | 1c | 1d | 1e |
|---|---|---|---|---|---|---|
| Final quantity of electricity (mAh/cm$^2$) | 0 | 1 | 1 | 0.9 | 1 | 1 |
| Initial quantity of active principle (mg/cm$^2$) | 5 | 5 | 1 | 1 | 1 | 0.5 |
| aXa activity/ml at 5 hours | 0.2 | 23 | 22 | 15 | 59 | 49 |
| Quantity of active principle at 5 hours (μg/cm$^2$) | 1 | 115 | 110 | 75 | 295 | 245 |
| aXa activity/ml at 22 hours | 0.3 | 30 | 28 | 20 | 70 | 62 |
| Quantity of active principle at 22 hours (μg/cm$^2$) | 1.5 | 150 | 140 | 110 | 390 | 310 |
| Quantity of active principle per mAh (μg/cm$^2$) | 1.5 | 150 | 140 | 125 | 390 | 310 |
| Utilization factor of the active principle (%)* | 0.03 | 3 | 14 | 11 | 39 | 62 |

*Utilization factor of the active principle = the ratio of the quantity of active principle at 22 hours to the initial quantity of active principle.

Reading Table IB shows that the passive transport of the pentasaccharide is very low, that there is a certain antinomy between the quantities of active principle passed per mAh and the depletion factors of the electrodes (utilization factor of the active principle or product efficiency) and that it is preferable to use thin reservoirs making it possible to reduce the quantity of active principle if it is desired to improve efficiency thereof, as can be seen on comparing Tests 1a and 1b.

It can also be seen, by comparing Tests 1d and 1b, that when a membrane according to the invention made of a polyether block amide and an electrode reservoir (secondary reservoir element) with a volume larger than the volume of the active principle reservoir (primary reservoir element) is interposed between the electrode and the reservoir of active principle, both the quantity of active principle administered per unit quantity of electricity and the active principle depletion factor of the donor electrode assembly are increased very substantially.

The choice of this combination makes it possible to achieve even higher depletion factors by using very thin reservoirs of active principle, as shown by Test 1e, by making optimum use of the very small quantities of active principle present per unit area.

It can also be seen that the membranes based on the mixture of cellulose acetate and POEG are much less effective than the membranes based on polyether block amide.

EXAMPLE 2

Administration in mini pigs of pentasaccharide sodium salt by iontophoresis at a set current density.

Specialists consider mini pigs of the YUCATAN strain to be an excellent animal model for studying the administration in man of medicaments by iontophoresis. This is because the skin structure of this animal is very similar to that of human skin.

The following tests were carried out on the aforementioned mini pig with the aim of comparing the administration by iontophoresis of the sodium salt of the pentasaccharide used in Example 1 with administration by subcutaneous injection.

For these tests, pairs of adhesive electrode assemblies were formed, each pair comprising a donor electrode assembly, equipped with a reversible negative electrode (active electrode) and containing the pentasaccharide to be administered, and a passive electrode assembly formed by a positive electrode (back electrode) in contact with a second reservoir element containing an arbitrary (i.e. indifferent) electrolyte.

Figure 2:
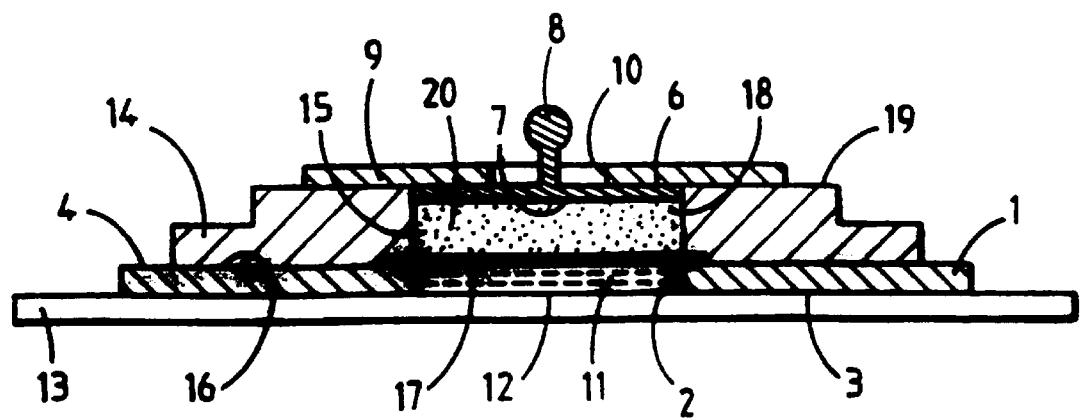

Each donor electrode assembly had a structure similar to one or other of the structures schematically represented, by way of non-limiting example, in the two figures of the appended drawing, in which:

FIG. 1 illustrates a reference electrode assembly formed by a reversible negative electrode in direct contact with a single reservoir element; and FIG. 2 illustrates a donor electrode assembly according to the invention, comprising a primary reservoir element and a secondary reservoir element, which are separated from one another by a selectively permeable membrane made of polyether block amide, and a negative electrode in direct contact with the secondary reservoir element.

Each reference electrode assembly schematically represented in FIG. 1 comprised a disc 1 of polyethylene foam having an axial cylindrical recess 2, the said disc comprising an adhesive face 3 and a nonadhesive face 4, each of the said faces having the shape of an annular area with a width of two centimeters. The end 5 of the recess in the disc, on the nonadhesive face side, was closed off by an electrode 6 having the form of a silver disc chloridized on one of its faces, the said disc having a cross-sectional area of 20 cm$^2$. The chloridized face 7 of the electrode disc was turned towards the interior of the recess. The nonchloridized face of the said disc had a contact connector 8 of the push-button type welded to the said face by means of an electronically conductive adhesive, and was pressed against a polyethylene foam support disc 9, coaxial with the disc 1 and having an axial recess 10 to allow access to the contact connector 8. The said support disc, having a diameter between that of the electrode 6 and the disc 1, was bonded adhesively onto the nonadhesive face of the latter disc. The recess 2 in the disc 1 was filled with a conducting, abosrbent porous material containing the pentasaccharide and forming a reservoir element 11. The adhesive face 3 of the disc 1 was coated with a pressure-sensitive adhesive designed to be applied to the skin, the said face 3 and the face 12 adjacent to the reservoir element 11 being initially covered with a peelable non-stick polyester protective film 13 which was removed before application to the skin.

Each donor electrode assembly according to the invention schematically represented in FIG. 2 comprised, on the one hand, a disc 1 of polyethylene foam having an axial, cylindrical recess 2 and, on the other hand, a stepped disc 14, also made of polyethylene foam, the said disc 14 being coaxial with the disc 1 and having a cylindrical recess 15 with the same diameter as the recess 2 in the disc 1. The said disc 1 comprised an adhesive face 3 and a nonadhesive face 4, each of the said faces having the shape of an annular area with a width of two centimeters. The stepped disc 14, with a diameter less than that of the disc 1, was adhesively bonded by one face 16 to the face 4 of the said disc 1. The recesses 2 and 15 were separated from one another by a selectively permeable membrane 17 made of polyether block amide, the said membrane being adhesively bonded by one face to the face 4 of the disc 1 and by another face to the face 16 of the stepped disc 14. The end 18, furthest away from the membrane, of the recess 15 in the stepped disc 14 was closed off by an electrode 6 having the shape of a silver disc chloridized on one of its faces, the said disc having a cross-sectional area of 20 cm$^2$. The chloridized face 7 of the electrode disc was turned towards the interior of the recess 15. The nonchloridized face of the said disc had a contact connector 8 of the push-button type welded to the said face by means of an electronically conducting adhesive, and was pressed against a polyethylene foam support disc 9, coaxial with the disc 1 and the stepped disc 14 and having an axial recess 10 to allow access to the contact connector 8. The said support disc, having a diameter between that of the electrode 6 and that of the face 19 of the stepped disc 14, was adhesively bonded to the said face. The recess 2 in the disc 1 was filled with a conducting, absorbent, porous material containing the pentasaccharide (primary electrolyte medium) and constituting a primary reservoir element 11. The recess 15 in the stepped disc 14 was filled with a conducting hydrogel 20 containing an arbitrary electrolyte and constituting a secondary reservoir element. The adhesive face 3 of the disc 1 was coated with a pressure-sensitive adhesive designed to be applied to the skin, the said face 3 and the face 12 adjacent to the primary reservoir element 11 being initially covered with a peelable non-stick polyester protective film 13 which was removed before application to the skin.

In the donor electrode assembly according to the invention, as well as in the reference donor assembly, the electrode 6 made of chloridized silver contained a quantity of silver chloride equivalent to 1.8 mAh/cm$^2$, thus allowing the electrode to sustain the quantity of electricity flowing through the electrodes over the duration of the iontophoretic treatment, namely 0.88 mAh/cm$^2$.

The primary electrolyte medium constituting the primary reservoir element 11 of the donor electrode assembly according to the invention, as well as the conducting, absorbent, porous material forming the reservoir element 11 of the reference electrode assembly, each consisted of a sheet of blotting paper made of cellulose fibres supplemented by polypropylene fibrils, having a surface area of 20 cm$^2$ and a thickness of 0.5 mm and being impregnated, to a level of 50 mg/cm$^2$, with an aqueous solution containing 2% by weight of pentasaccharide. Each reservoir element 11 contained in total 1 g of solution, i.e. 20 mg of pentasaccharide over 20 cm$^2$ of active surface (1 mg/cm$^2$). 20 mg of pentasaccharide were therefore employed in total per animal.

The conducting hydrogel 20 forming the secondary reservoir element had a thickness of 3 mm and consisted of a hydrogel based on agarose containing an NaCl solution with 0.1 g/l of this compound.

The selectively permeable membrane separating the recesses 2 and 15 of the donor electrode assembly according to the invention, that is to say separating the primary 11 and secondary 20 reservoir elements of the said electrode assembly, consisted of a 50 μm thick film of the polyether block amide PEBAX MV 1041 defined in Example 1.

In each passive electrode assembly, the positive electrode (back electrode) made of chloridized silver contained a quantity of silver chloride equivalent to 0.1 mAh/cm$^2$ and the reservoir element associated with this electrode consisted of a sheet of blotting paper made of cellulose fibres supplemented by polypropylene fibrils having a surface area of 20 cm$^2$ and a thickness of 0.5 mm and was impregnated with an aqueous solution of NaCl to contain 6% by weight of this salt.

An electric signal generator which could be connected to the electrodes of each pair of electrode assemblies, made it possible to deliver a continuous electric signal of controlled intensity between the said electrodes.

Five days before each test, the animals were catheterized in the two jugulars, as is well known for any experimentation in medicament administration, in order to make it possible to take regular blood samples intended for assaying the antifactor Xa activities and thereby to evaluate the quantities of active principle that pass through the skin to enter the circulatory system and therefore to check the effectiveness of the iontophoretic treatment.

The animals, fasted from the day before the experiments, were placed in specialized hammocks. A pair of electrode assemblies, with their peelable protective film removed beforehand, were adhesively bonded by simple pressure on the back of each animal, cleaned beforehand using a wet tissue, on either side of the spinal column, and, using cables fitted with clips designed for the contact connectors fitted for this purpose, the negative electrode of the donor electrode assembly was connected to the negative pole of the generator and the back electrode of the passive electrode assembly was connected to the positive pole of the said generator.

The generator was used to set up a current of 2.2 mA (i.e. a current density of 0.11 mA/cm$^2$) between the positive and negative electrodes of each pair of electrode assemblies adhesively bonded to the animal, for a period of 8 hours and various blood samples were taken with an H STAGO® diatube periodically until 30 hours after the start of each experiment, i.e. 22 hours after the end of the iontophoretic treatment. Each iontophoretic test was repeated on four male mini pigs with an average weight of 12.1 kg.

Further to the test according to the invention and the reference test of administration of the pentasaccharide active principle by iontophoresis carried out as described above (Test 2b according to the invention and reference Test 2c), comparative Tests 2a and 2d were also carried out as follows, each test being repeated on four mini pigs, as in the case of the iontophoretic administration:

Test 2a: fitting the electrode assemblies as in the iontophoresis Tests 2b and 2c, but without applying a current (determination of the passive transport).

Test 2d: subcutaneous injection of 0.200 mg/kg of pentasaccharide in injectable solution.

In these Tests 2a and 2d, a number of blood samples were taken periodically, up to 30 hours after the start of each experiment, as in the case of the iontophoretic treatment in Tests 2b and 2c.

The plasma levels of the various blood samples, expressed in "Golden Standard" units of antifactor Xa, are indicated in Table II for the purpose of comparison of the average plasma levels obtained for animals of the same strain and with the same weight treated with the same active principle under the conditions of the tests according to the invention (Test 2b) and of the comparative tests (Tests 2a, 2c and 2d).

TABLE II

| | Antifactor Xa units/ml Test | | | |
|---|---|---|---|---|
| Duration (hours) | 2a | 2b | 2c | 2d |
| 0 | 0 | 0 | 0 | 0 |
| 0.25 | 0 | 0.07 | 0.03 | 0.11 |
| 0.50 | 0 | 0.14 | 0.05 | 0.13 |
| 1.00 | 0 | 0.36 | 0.09 | 0.17 |
| 2.00 | 0 | 0.81 | 0.13 | 0.22 |
| 4.00 | 0 | 1.3 | 0.27 | 0.26 |
| 6.00 | 0 | 0.98 | 0.29 | 0.24 |
| 8.00 | 0 | 1 | 0.35 | 0.15 |

TABLE II-continued

| | Antifactor Xa units/ml Test | | | |
|---|---|---|---|---|
| Duration (hours) | 2a | 2b | 2c | 2d |
| 10.00 | 0 | 0.79 | 0.34 | 0.12 |
| 12.00 | 0 | 0.61 | 0.14 | 0.06 |
| 16.00 | 0 | 0.38 | 0.11 | 0.06 |
| 24.00 | 0 | 0.12 | 0.08 | 0.00 |
| 30.00 | 0 | 0.04 | 0.01 | 0.00 |
| mAh | 0 | 0.88 | 0.88 | 0 |
| Weight of the mini pigs | 12.3 kg | 11.9 kg | 12.2 kg | 12 kg |
| PS administered (mg) | 0 | 13.2 | 4.2 | 2.4 |
| PS administered (mg/cm$^2$) | 0 | 0.66 | 0.21 | |
| PS administered (mg/mAh.cm$^2$) | | 0.755 | 0.233 | |
| Bioavailability (%) | 0 | 66 | 20 | |

Comparing the results presented in Table II shows that the iontophoretic treatment carried out according to the invention leads to plasma levels, expressed in terms of antifactor Xa, more than three times higher than those which are obtained iontophoretically by using an active principle reservoir element identical to that used according to the invention, but without requiring the structure with two reservoirs which are separated by the polyether block amide membrane.

In particular, the bioavailability, that is to say the proportion of active principle actually administered in relation to the quantities of active principle in the donor electrode assemblies, is approximately 66% in the iontophoretic treatment according to the invention (Test 2b) as opposed to only about 20% in the reference iontophoretic treatment (Test 2c).

It can also be seen that the bioavailability for the in-vivo tests is higher than the utilization factors which were obtained for the in-vitro tests (Example 1).

EXAMPLE 3

Administration to mini pigs of the sodium salt of a low molecular mass heparin by iontophoresis with set current density.

The tests described in this example were carried out on YCATAN strain mini pigs with the aim of comparing the administration, by iontophoresis, of an active principle consisting of the sodium salt of a low molecular mass heparin with the administration of the said active principle passively or by subcutaneous injection.

The active principle was obtained as described in citation EP-A-0181252 and had an average molecular mass ranging from 4000 to 5000 and an antifactor Xa activity, expressed in international units (abbreviated to IU) equal to 100 IU/mg.

Depending on the tests, the active principle was administered passively (Test 3a) by iontophoresis according to the invention (Test 3b), by reference iontophoresis (Test 3c) or by subcutaneous injection (Test 3d).

For the tests on iontophoresis or passive administration, adhesive electrode assembly pairs were formed, each pair comprising a donor electrode assembly, equipped with a reversible negative electrode (active electrode) containing the active principle to be administered, and a passive electrode assembly formed by a positive electrode (back electrode) in contact with a second reservoir element containing an arbitrary electrolyte.

The donor electrode assembly of each electrode assembly pair had a structure similar to that schematically represented in FIG. 2, in the case of Test 3b (iontophoresis according to the invention), or to that represented in FIG. 1 in the case of Test 3c (reference iontophoresis).

In the donor electrode assembly according to the invention, as well as in the reference donor assembly, the electrode 6 of chloridized silver had a surface area of 25 cm$^2$ and contained a quantity of silver chloride equivalent to 2.4 mAh/cm$^2$, thus allowing the electrode to sustain the quantity of electricity flowing through the electrodes over the duration of the iontophoretic treatment, namely 1.92 mAh/cm$^2$.

The primary electrolyte medium constituting the primary reservoir element 11 of the donor electrode assembly according to the invention, as well as the conducting, absorbent, porous material forming the reservoir element 11 of the reference electrode assembly, each consisted of a sheet of blotting paper made of cellulose fibres supplemented by polypropylene fibrils, having a surface area of 25 cm$^2$ and a thickness of 0.5 mm and being impregnated, to a level of 50 mg/cm$^2$, with an aqueous solution containing 5% by weight of active principle. Each reservoir element 11 contained in total 1.25 g of solution, i.e. 62.5 mg of active principle over 25 cm$^2$ of active surface (2.5 mg/cm$^2$). 62.5 mg of active principle were therefore employed in total per animal.

The conducting hydrogel 20 forming the secondary reservoir element had a surface area of 25 cm$^2$ and a thickness of 2 mm and consisted of a hydrogel based on agarose containing an NaCl solution with 0.1 g/l of this compound, the quantity of hydrogel representing 200 mg/cm$^2$.

The selectively permeable membrane separating the recesses 2 and 15 of the donor electrode assembly according to the invention, that is to say separating the primary 11 and secondary 20 reservoir elements of the said electrode assembly, consisted of a 50 µm thick film of the polyether block amide PEBAX MV 1041 defined in Example 1.

In each passive electrode assembly, the positive electrode (back electrode) made of chloridized silver had a surface area of 25 cm$^2$ and contained a quantity of silver chloride equivalent to 0.1 mAh/cm$^2$. The reservoir element associated with this electrode consisted of an agarose hydrogel having a surface area of 25 cm$^2$ and a thickness of 0.2 mm (200 mg/cm$^2$), the said hydrogel containing a 2% by weight NaCl salt solution.

An electric signal generator which could be connected to the electrodes of each pair of electrode assemblies, made it possible to deliver a continuous electric signal of controlled intensity between the said electrodes.

The animals were prepared for the tests as indicated in Example 2. In addition, the pairs of electrodes were fitted to the animals, for iontophoretic administration, as described in the said Example 2.

For carrying out the iontophoresis tests according to the invention (Test 3b) and reference (Test 3c), the generator was used to set up a current of 4 mA (i.e. a current density of 0.16 mA/cm$^2$) between the positive and negative electrodes of each pair of electrode assemblies adhesively bonded to the animal, for a period of 12 hours, and various blood samples were taken with an H STAGO® diatube periodically until 30 hours after the start of each experiment, i.e. 18 hours after the end of iontophoretic treatment. Each iontophoretic test was repeated on four male mini pigs.

Further to the test according to the invention (Test 3b) and the reference test (Test 3c) on administration of the active principle by iontophoresis carried out as described above, comparative Tests 3a and 3d were also carried out as follows, each test being repeated on four mini pigs, as in the case of the iontophoretic administration:

Test 3a: fitting of the electrode assemblies as in the iontophoresis Tests 3b and 3c, but without applying a current (determination of the passive transport).

Test 3d: subcutaneous injection of 4.5 mg of active principle in injectable solution.

In these Tests 3a and 3d, a number of blood samples were taken periodically, up to 30 hours after the start of each experiment, as in the case of the iontophoretic treatment in Tests 3b and 3c.

The plasma levels of the various blood samples, expressed in international units of antifactor Xa, are indicated in Table III for the purpose of comparison of the average plasma levels obtained for animals of the same strain and of the same weight treated with the same active principle under the conditions of the tests according to the invention (Test 3b) and the comparative tests (Tests 3a, 3c and 3d).

TABLE III

|  | Antifactor Xa activity (I.U./ml) Test | | | |
| --- | --- | --- | --- | --- |
| Duration (hours) | 3a | 3b | 3c | 3d |
| 0 | 0 | 0 | 0 | 0 |
| 0.50 | 0 | 0.09 | 0.03 | 0.41 |
| 1.00 | 0 | 0.23 | 0.09 | 2.64 |
| 1.50 | 0 | 0.34 | 0.12 | 3.04 |
| 2.00 | 0 | 0.42 | 0.14 | 3.08 |
| 3.00 | 0 | 0.46 | 0.13 | 3.44 |
| 4.00 | 0 | 0.58 | 0.21 | 3.39 |
| 6.00 | 0 | 0.68 | 0.26 | 2.71 |
| 8.00 | 0 | 0.72 | 0.33 | 2.28 |
| 10.00 | 0 | 0.68 | 0.29 | 0.21 |
| 12.00 | 0 | 0.74 | 0.26 | 0.12 |
| 16.00 | 0 | 0.18 | 0.11 | 0.00 |
| 24.00 | 0 | 0.06 | 0.04 | 0.00 |
| 30.00 | 0 | 0.00 | 0.02 | 0.00 |
| mAh | 0 | 1.92 | 1.92 | 0 |
| Average weight of the mini pigs | 12.4 kg | 13.6 kg | 11.9 kg | 13 kg |
| PA administered (mg) | 0 | 8.214 | 3.046 | 4.5 |
| PA administered (mg/cm$^2$) | 0 | 0.328 | 0.122 | |
| PA administered (mg/mAh.cm$^2$) | | 0.171 | 0.063 | |
| Bioavailability (%) | 0 | 13.1 | 4.9 | |

Comparing the results presented in Table III shows that the iontophoretic treatment carried out according to the invention leads to plasma levels, expressed in terms of antifactor Xa, approximately three times higher than those which are obtained iontophoretically by using an active principle reservoir element identical to that used according to the invention, but without requiring the structure with two reservoirs which are separated by the polyether block amide membrane.

In particular, the bioavailability, that is to say the proportion of active principle actually administered in relation to the quantities of active principle in the donor electrode assemblies, is approximately 13.1% in the iontophoretic treatment according to the invention (Test 3b) as opposed to only about 4.9% in the reference iontophoretic treatment (Test 3c).

What is claimed is:

1. Iontophoresis device, for transcutaneous administration of an active principle to a subject, comprising (a) a first electrode assembly, called the donor electrode assembly, consisting of a first electrode called the active electrode, a primary reservoir element designed to contain a primary electrolyte medium containing the active principle in an at least partially ionized form or in a neutral form in order to ensure, when it is placed in contact with an area of the subject's skin, ionically conducting continuity between the said first electrode and the said area, and a membrane made of polymer material in contact, via one face, with the first electrode and, via another face, with the primary reservoir element, the said membrane being selectively permeable to ions and molecules of sizes smaller than a chosen threshold, (b) a second electrode assembly consisting either (i) of a second electrode, called the back electrode, or preferably (ii) of a second electrode of this type in contact with a reservoir element, called the back electrode, designed to contain at least one electrolyte medium and to ensure, when it is placed in contact with a portion of the subject's skin, ionically conducting continuity between the second electrode and the said portion and (c) an electric signal generator which can be connected to each of the said first and second electrodes in such a way that the first electrode has the same polarity as the ions of the active principle or a positive polarity if the said active principle is neutral and that the second electrode has a polarity opposite to that of the first electrode, wherein in the said device the polymer material constituting the selectively permeable membrane consists of at least one polyether block amide formed by identical or different units corresponding to the formula

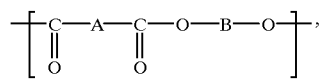

in which A is a polyamide sequence derived, by losing its COOH groups, from a dicarboxylic polyamide having a COOH group at each of the ends of its chain, and B is a polyoxyalkylene sequence derived, by losing two hydroxyl groups, from a polyoxyalkylene glycol whose chain is formed by oxyalkylene units having 2 to 4 carbon atoms and has an OH group at each of its ends, the said polyether block amide having a number-average molecular mass of between 10,000 and 300,000 and containing a proportion by weight of polyamide sequences A of between 35% and 90%.

2. Device according to claim 1, wherein the polyether block amide of which the membrane is formed has a number-average molecular mass of between 10,000 and 200,000.

3. Device according to claim 1 wherein the polyether block amide of which the membrane is formed has a proportion by weight of polyamide sequences A of between 45% and 85%.

4. Device according to one of claim 3, wherein the dicarboxylic polyamide from which the polyamide sequence A derives is obtained by polycondensation, in the presence of a dicarboxylic acid having 4 to 20 carbon atoms in its molecule, of one or more monomers selected from he group formed by lactams and amino acids having 4 to 6 carbon atoms in their molecules and the combinations of one or more diamines having 4 to 16 carbon atoms in their molecules with one or more dicarboxylic acids having 4 to 18.

5. Device according to claim 4, wherein the dicarboxylic polyamide from which the polyamide sequence A derives is obtained from one or more monomers chosen from caprolactam, cenantholactam, dodecalactam, undecanolactam, decanolactam, 11-amino undecanoic acid and 12-amino dodecanoic acid.

6. Device according to claim 4, wherein the dicarboxylic polyamide from which the polyamide sequence A derives is produced by polycondensation of hexamethylene diamine with adipic acid, azelaic acid, sebacic acid or 1,12-dodecanedioic acid or by polycondensation of nonamethylene diamine with adipic acid.

7. Device according to claim 1, wherein the number-average molecular masses of the sequences A derived from the dicarboxylic polyamides lie between 300 and 15,000.

8. Device according to claim 1, wherein the polyoxyalkylene glycols from which the sequence B of the units constituting the polyether block amide derives are polymers consisting of one or more of the repeat units

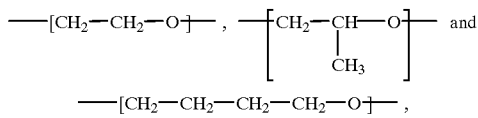

selected from the group consisting of polyoxyethylene glycols, polyoxypropylene glycols, polyoxytetramethylene glycols, copoly(oxyethylene/oxypropylene)glycols, copoly(oxyethylene/-oxytetramethylene)glycols, copoly(oxyethylene/-oxypropylene/oxytetramethylene) glycols and mixtures of such polyoxyalkylene glycols and/or their copolymers.

9. Device according to claim 1, wherein the number-average molecular masses of the sequences B are between 100 and 6000.

10. Device according to claim 1, wherein the polyether block amide membrane has a thickness of between 10 μm and 200 μm.

11. Device according to claim 1, wherein the primary reservoir element of the first electrode assembly has a thickness of between 50 μm and 1000 μm.

12. Device according to claim 1, wherein the first electrode assembly is also provided with a secondary reservoir element containing an arbitrary electrolyte, the said secondary reservoir element being arranged between the electrode of the said assembly and the polyether block amide membrane so as to be in contact with each of them.

13. Device according to claim 12, wherein the volume of the secondary reservoir element is greater than or equal to the volume of the primary reservoir element.

14. Device according to claim 1, wherein at least the electrode of the first electrode assembly is an electrode which can be consumed electrochemically when the current flows during operation of the ionophoresis device, the consumable electrode being a reversible electrode.

15. Device according to claim 14, for administering a given total quantity of the active principle to the subject, wherein one or other of the electrodes is designed to form an electrode, called the limiting electrode, formed by a limited quantity of an electrochemically consumable material combined either with an electronically conducting support or an insulating support, the said electrochemically consumable material being either an electrochemically reducible metal compound when the limiting electrode is a cathode or a metal consumable by electrochemical oxidation when the limiting electrode is an anode, and the said electronically conducting support being made of a material which resists corrosion by the electrolyte associated with the limiting electrode in the absence of current and which has, when the limiting electrode is a cathode, a hydrogen overpotential in the presence of the said electrolyte at least equal to that of aluminium or which is not consumable by electrochemical oxidation when the limiting electrode is an anode, while the said limited quantity of electrochemically consumable material is chosen so that the quantity of electricity needed to consume it electrochemically corresponds to the quantity of electricity needed to administer the given total quantity of active principle to the subject so that the flow of current between the electrodes is substantially interrupted when the consumable material of the limiting electrode has been consumed, and the active principle is initially present in the primary reservoir element in a quantity greater than the given total quantity to be administered to the subject.

16. Device according to claim 1, wherein the electrical generator applies between the electrodes of the said device an intensiometric electric signal or a potentiometric signal or both types of signals, the said electric signal being continuous or pulsed and permanent or intermittent, with or without temporary polarity inversion, and having a frequency ranging from 0 to 500 kHz.

17. Device according to claim 16, wherein the electric signal is a pulsed signal having a duty cycle ranging from 0.05 to 0.95.

18. Device according to claim 16, wherein the electric signal applied between the electrodes has an average voltage chosen between 0.1 and 50 volts so that the density of the average current generated between the said electrodes has a value less than 0.50 mA/cm$^2$.

19. Device according to claim 1, wherein the primary electrolyte medium present in the primary reservoir element of the first electrode assembly consists of an aqueous solution or of an adhesive or nonadhesive hydrogel containing the active principle to be administered in an at least partially ionized form or in a neutral form, or is in the form of a hydratable solid consisting of a selfadhesive or non-self-adhesive matrix made of a hydrophobic material in which one or more water-soluble or hydrophilic polymers and the active principle to be administered are dispersed.

20. Device according to claim 12, wherein the arbitrary electrolyte contained in the secondary reservoir element of the first electrode assembly consists of an aqueous solution or a hydrogel containing one or more pharmaceutically acceptable salts which can be ionized in the aqueous phase, or is in the form of a hydratable solid formed by a hydrophobic polymer matrix in which one or more hydrophilic polymers and the ionizable salt or salts are dispersed, or consists of a hydrophilic absorbent matrix containing the ionizable salt or salts in the dispersed state.

21. Device according to claim 19, wherein the primary reservoir element and the secondary reservoir element are in the form of hydratable solids, and in that the said primary and secondary reservoir elements are assembled dry with the membrane and the associated electrode to form a first electrode assembly in the nonhydrated state.

22. Device according to claim 1, wherein the selectively permeable membrane prevents the migration of ions and molecules having molecular masses higher than 100 daltons.

23. Device according to claim 1, wherein the second electrode assembly has a structure similar to that of the first electrode assembly, and in that the electrode of each of the said assemblies is a reversible consumable electrode based on the Ag/AgCl pair.

24. Device according to claim 19, wherein the concentration of active principle in the aqueous phase of the primary electrolyte medium of the primary reservoir element is between 0.2% by weight of the aqueous phase and the saturation concentration of the said aqueous phase.

25. Donor electrode assembly, in particular for an iontophoresis device, comprising an active electrode, a primary reservoir element, designed, on the one hand, to contain a primary electrolyte medium containing an active principle in an at least partially ionized form or in a neutral form and, on the other hand, in order to ensure, when it is placed in contact with an area of the subject's skin, ionically conducting continuity between the said electrode and the said area, and a membrane made of polymer material in contact, via one face, with the electrode and, via another face, with the primary reservoir element, the said membrane being selectively permeable to ions and molecules of sizes smaller than a chosen threshold, the said donor assembly being wherein the polymer material constituting the selectively permeable membrane consists of at least one polyether block amide formed by identical or different units corresponding to the formula

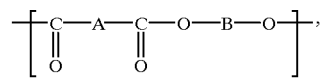

in which A is a polyamide sequence derived, by losing its COOH groups, from a dicarboxylic polyamide having a COOH group at each of the ends of its chain, and B is a polyoxyalkylene sequence derived, by losing two hydroxyl groups, from a polyoxyalkylene glycol whose chain is formed by oxyalkylene units having 2 to 4 carbon atoms and has an OH group at each of its ends, the said polyether block amide having a number-average molecular mass of between 10,000 and 300,000 and containing a proportion by weight of polyamide sequences A of between 35% and 90%.

26. Assembly according to claim 25, wherein the polyether block amide of which the membrane is formed has a number-average molecular mass of between 10,000 and 200,000.

27. Assembly according to claim 25 wherein the polyether block amide of which the membrane is formed has a proportion by weight of polyamide sequences A of between 45% and 85%.

28. Assembly according to claim 25, wherein the dicarboxylic polyamide from which the polyamide sequence A derives is obtained by polycondensation, in the presence of a dicarboxylic acid having 4 to 20 carbon atoms in its molecule, of one or more monomers selected from the group formed by lactams and amino acids having 4 to 16 carbon atoms in their molecules and the combinations of one or more diamines having 4 to 16 carbon atoms in their molecules with one or more dicarboxylic acids having 4 to 18 carbon atoms in their molecules.

29. Assembly according to claim 28, in that the dicarboxylic polyamide from which the polyamide sequence A derives is obtained from one or more monomers chosen from caprolactam, oenantholactam, dodecalactam, undecanolactam, decanolactam, 11-amino undecanoic acid and 12-amino dodecanoic acid, the said polyamide being, in particular, like polyamide-6, polyamide-11, polyamide-12, copolyamide-6/11 or copolyamide-6/12.

30. Assembly according to claim 28, wherein the dicarboxylic polyamide from which the polyamide sequence A derives is produced by polycondensation of hexamethylene diamine with adipic acid, azelaic acid, sebacic acid or 1,12-dodecanedioic acid or by polycondensation of nonamethylene diamine with adipic acid.

31. Assembly according to claim 25, wherein the number-average molecular masses of the sequences A derived from the dicarboxylic polyamides lie between 300 and 15,000.

32. Assembly according to claim 25, wherein the polyoxyalkylene glycols from which the sequence B of the units constituting the polyether block amide derives are polymers consisting of one or more of the repeat units

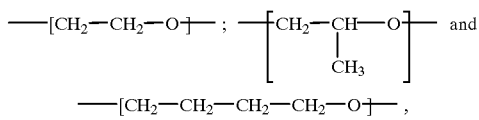

selected from the group consisting of polyoxyethylene glycols, polyoxypropylene glycols, polyoxytetramethylene glycols, copoly(oxyethylene/oxypropylene) glycols, copoly (oxyethylene/oxytetramethylene) glycols, copoly (oxyethylene/oxypropylene/oxytetramethylene) glycols and mixtures of such polyoxyalkylene glycols and/or their copolymers.

33. Assembly according to claim 25, wherein the number-average molecular masses of the sequences B are between 100 and 6000.

34. Assembly according to claim 25, wherein the polyether block amide membrane has a thickness of between 10 μm and 200 μm.

35. Assembly according to claim 25, wherein the primary reservoir element has a thickness of between 50 μm and 1000 μm.

36. Assembly according to claim 25, wherein it is also provided with a secondary reservoir element containing an arbitrary electrolyte, the said secondary reservoir element being arranged between the electrode of the said assembly and the polyether block amide membrane so as to be in contact with each of them.

37. Assembly according to claim 36, wherein the volume of the secondary reservoir element is greater than or equal to the volume of the primary reservoir element.

38. Assembly according to claim 25, wherein its electrode is an electrochemically consumable electrode, the said electrode being a reversible electrode.

39. Assembly according to claim 38, wherein the said consumable electrode is designed to form an electrode, called the limiting electrode, formed by a limited quantity of an electrochemically consumable material combined either with an electronically conducting support or an insulating support, the said electrochemically consumable material being either an electrochemically reducible metal compound when the limiting electrode is a cathode or a metal consumable by electrochemical oxidation, in particular a metal such as Al, Mg, Zn or Ag, when the limiting electrode is an anode, and the said electronically conducting support being made of a material which resists corrosion by the electrolyte associated with the limiting electrode in the absence of current and which has, when the limiting electrode is a cathode, a hydrogen overpotential in the presence of the said electrolyte at least equal to that of aluminium or which is not consumable by electrochemical oxidation when the limiting electrode is an anode, while the said limited quantity of electrochemically consumable material is chosen so that the quantity of electricity needed to consume it electrochemically corresponds to the quantity of electricity needed to administer a given total quantity of an active principle to a subject, so that the flow of current between the electrode of the said assembly and a back electrode is substantially interrupted when the consumable material of the limiting electrode has been consumed, and the active principle is initially present in the primary reservoir element in a quantity greater than the given total quantity to be administered to the subject.

40. Assembly according to claim 25, wherein the primary electrolyte medium present in the primary reservoir element of the said assembly consists of an aqueous solution or of an adhesive or nonadhesive hydrogel containing the active principle to be administered in an at least partially ionized form or in a neutral form, or is in the form of a hydratable solid consisting of a self-adhesive or non-self-adhesive matrix made of a hydrophobic polymer material in which one or more water-soluble or hydrophilic polymers and the active principle to be administered are dispersed.

41. Assembly according to claim 36, wherein the arbitrary electrolyte contained in the secondary reservoir element of the said assembly consists of an aqueous solution or a hydrogel containing one or more pharmaceutically acceptable salts which can be ionized in the aqueous phase, or is in the form of a hydratable solid formed by a hydrophobic polymer matrix in which one or more hydrophilic polymers and the ionizable salt or salts are dispersed, or consists of a hydrophilic absorbent matrix containing the ionizable salt or salts in the dispersed state.

42. Assembly according to claim 40, wherein the primary reservoir element and the secondary reservoir element are in the form of hydratable solids, and in that the said primary and secondary reservoir elements are assembled dry with the membrane and the associated electrode to form the said assembly in the nonhydrated state.

43. Assembly according to claim 25, wherein the selectively permeable membrane prevents the migration of ions and molecules having molecular masses higher than 100 daltons.

44. Assembly according to claim 40, wherein the concentration of active principle in the aqueous phase of the primary electrolyte medium of the primary reservoir element is between 0.2% by weight of the aqueous phase and the saturation concentration of the said aqueous phase.

* * * * *